United States Patent
Janzig

(10) Patent No.: US 10,071,253 B2
(45) Date of Patent: Sep. 11, 2018

(54) IMPLANTABLE DEVICE WITH INTERNAL LEAD CONNECTOR

(71) Applicant: MEDTRONIC, INC., Minneapolis, MN (US)

(72) Inventor: Darren A. Janzig, Center City, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/210,889

(22) Filed: Mar. 14, 2014

(65) Prior Publication Data

US 2014/0277217 A1 Sep. 18, 2014

Related U.S. Application Data

(60) Provisional application No. 61/789,257, filed on Mar. 15, 2013.

(51) Int. Cl.
*A61N 1/375* (2006.01)

(52) U.S. Cl.
CPC .................. *A61N 1/3752* (2013.01)

(58) Field of Classification Search
CPC .......................... A61N 1/3605; A61N 1/3752
USPC ............................... 607/2, 116, 36
See application file for complete search history.

(56) References Cited

U.S. PATENT DOCUMENTS

| | | | |
|---|---|---|---|
| 4,262,982 A | 4/1981 | Kenny | |
| 4,934,366 A | 6/1990 | Truex | |
| 7,515,964 B1 | 4/2009 | Alexander | |
| 7,563,141 B2 | 7/2009 | Alexander | |
| 7,711,427 B2 | 5/2010 | Janzig | |
| 7,711,428 B2 | 5/2010 | Janzig | |
| 7,890,175 B1 | 2/2011 | Rey | |
| 8,019,420 B2* | 9/2011 | Hine et al. | 607/37 |
| 8,065,008 B2* | 11/2011 | Sommer | A61N 1/3752 607/37 |
| 8,131,370 B2 | 3/2012 | Janzig | |
| 8,738,141 B2 | 5/2014 | Smith | |
| 2004/0176816 A1* | 9/2004 | Singhal et al. | 607/45 |
| 2005/0004620 A1* | 1/2005 | Singhal | A61B 5/076 607/45 |
| 2007/0179553 A1 | 8/2007 | Iyer | |
| 2014/0277216 A1 | 9/2014 | Janzig | |
| 2014/0277218 A1 | 9/2014 | Janzig | |

FOREIGN PATENT DOCUMENTS

WO    WO 00/24461    5/2000

OTHER PUBLICATIONS

International Search Report and Written Opinion for PCT/US2014/027215 dated Jul. 17, 2014 (9 pages).

* cited by examiner

*Primary Examiner* — Alyssa M Alter
(74) *Attorney, Agent, or Firm* — Mueting, Raasch & Gebhardt, P.A.

(57) ABSTRACT

An implantable active medical device includes a hermetic housing defining an exterior surface and a hermetic cavity of an implantable active medical device. An elongate lead connector extends into the hermetic cavity. The elongate lead connector includes a closed end, an open end extending through and hermetically joined to the hermetic housing, an outer surface at least partially defining the hermetic cavity, and an inner surface defining a lead aperture.

16 Claims, 3 Drawing Sheets

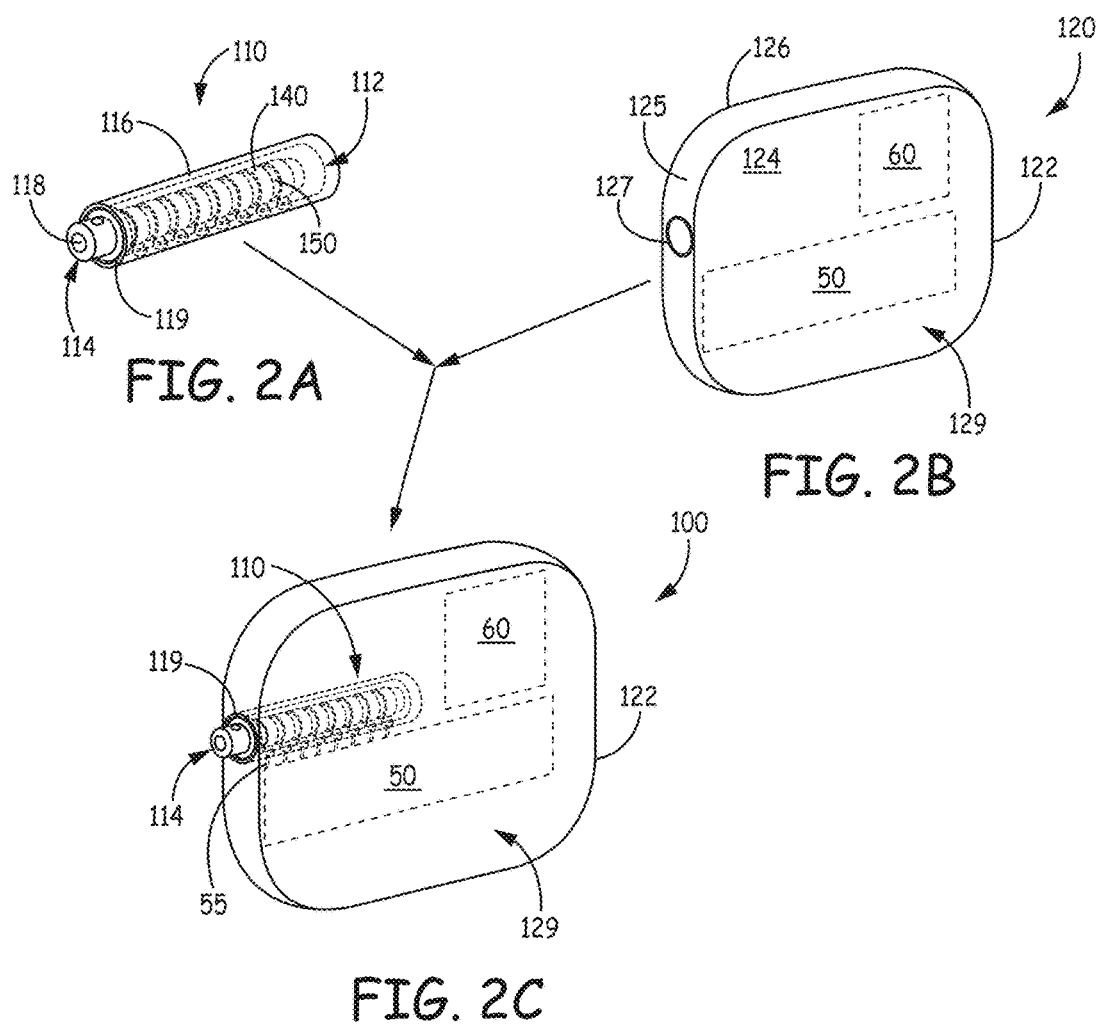

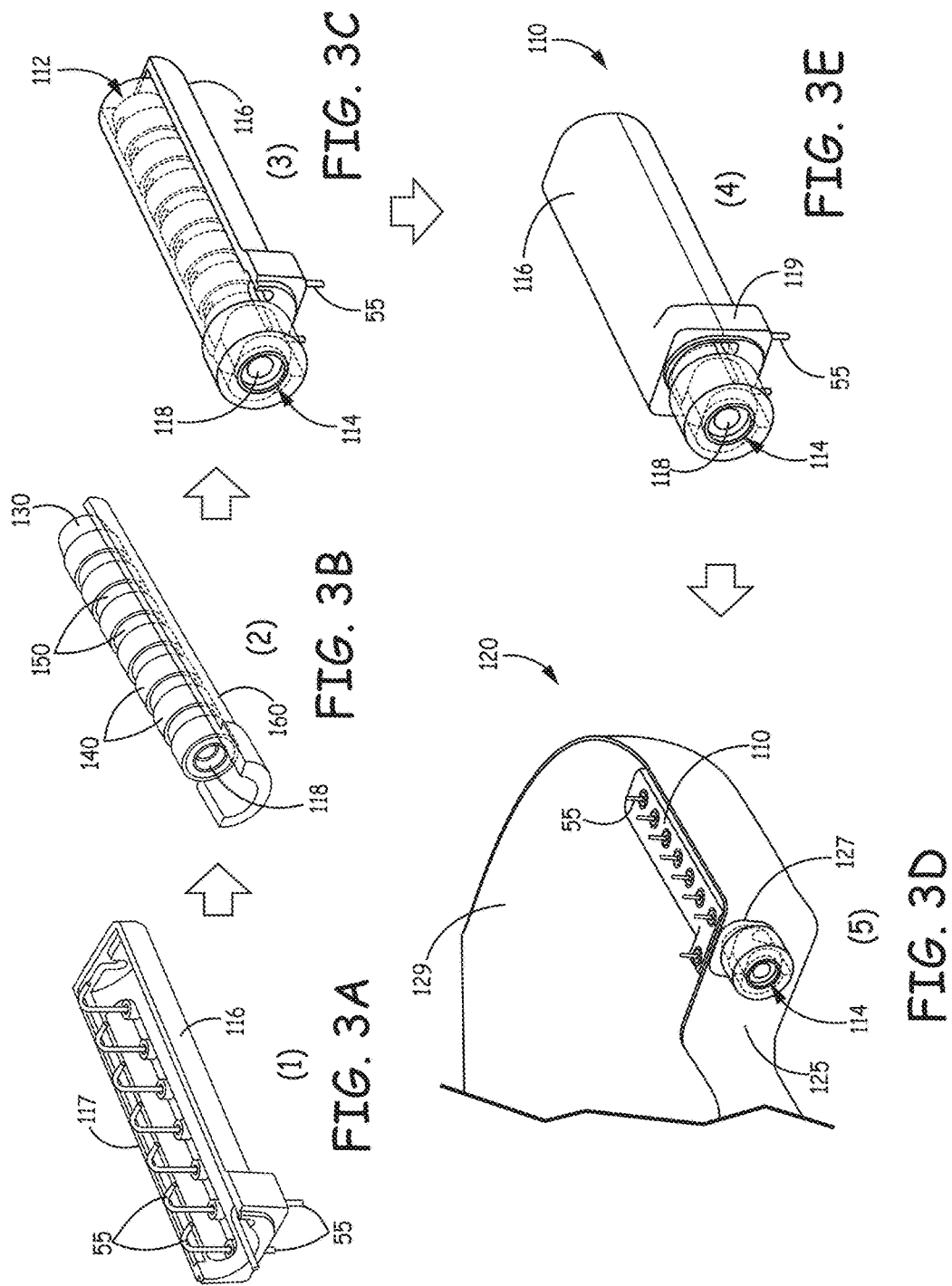

IMPLANTABLE DEVICE WITH INTERNAL LEAD CONNECTOR

CROSS-REFERENCE

This application claims the benefit of U.S. Provisional Application Ser. No. 61/789,257, filed Mar. 15, 2013, the disclosure of which is incorporated herein by reference.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case within a lead connector housing or block attached to the exterior of the housing or case. The lead connector block (may also be known as connector header) is often affixed to the hermetically sealed housing with brackets, metal solder, laser or resistance welding, pins, screws, and/or a medical grade adhesive and other types of fasteners. The function of the lead connector block is to electrically and mechanically couple the electronic pulse generator with the therapy lead. The lead connector block is typically attached to the exterior of the hermetically sealed housing and is significant to defining the overall device shape and volume. Most often with each new device design, a new lead connector block must also be designed requiring substantial project resources and project schedule.

The electronics within the hermetically sealed housing are conductively coupled to the lead connector block via an electrical feedthrough assembly. Electrical feedthroughs serve the purpose of providing a hermetically sealed conductive path extending between the interior of a hermetically sealed container and a point outside the hermetically sealed housing that ultimately connects to the lead contacts within the connector header. The conductive path through the feedthrough usually includes a conductor pin or terminal that is electrically insulated from the hermetically sealed housing and hermetically bonded to a feedthrough housing or ferrule. The feedthrough housing is hermetically assembled to the device housing most often by laser welding. The feedthrough assembly can be one or more discrete feedthroughs, an array for feedthroughs as an assembly, or any other combination. While this arrangement has proven to be highly reliable, it involves a variety of expensive manufacturing processes and parts that necessarily increase the cost and overall volume of the resulting product. The connector housing assembly typically partially or substantially defines the overall shape of the device and requires extensive resources and development time and schedule with each new generation of devices. The method of attachment to the device exterior also requires significant development time and resources.

Ongoing efforts by the industry to reduce the size of the implantable device are desired. Early implantable pacemakers back in the 1960's were about the size of a hockey puck. With advances in microelectronics and integrated circuitry, significantly more features and capabilities have been embodied in implantable active medical devices that can be very small. Nonetheless, efforts to further reduce the size of implantable active medical devices continue in the industry.

BRIEF SUMMARY

The present disclosure relates to an implantable medical device having a hermetic housing with an internal lead connector that extends into the hermetic housing.

In one illustrative embodiment, an implantable active medical device includes a hermetic housing defining an exterior surface and a hermetic cavity of an implantable active medical device. An elongate lead connector extends into the hermetic cavity. The elongate lead connector includes a closed end, an open end extending through and hermetically joined to the hermetic housing, an outer surface at least partially defining the hermetic cavity, and an inner surface defining a lead aperture.

In another illustrative embodiment, an implantable active medical device includes a hermetic housing defining an exterior surface and a hermetic cavity volume of an implantable active medical device. An elongate lead connector extends into the hermetic cavity. The elongate lead connector has a closed end, an open end extending through and hermetically joined to the hermetic housing, an outer surface, and an inner surface defining a lead aperture. The elongate lead connector has a connector volume and the hermetic cavity volume is reduced by an amount substantially equal to the connector volume when the elongate lead connector is assembled within the implantable active medical device.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which:

FIG. 2A is a schematic perspective view of an illustrative elongate lead connector;

FIG. 2B is a schematic perspective view of an illustrative hermetic housing of an implantable active medical device;

FIG. 2C is a schematic perspective view of the illustrative elongate lead connector of FIG. 2A assembled into the hermetic housing of an implantable active medical device of FIG. 2B; and FIGS. 3A-3E are schematic perspective views of a method of forming an elongate internal connector and disposing it within a hermetic cavity of the implantable active medical device.

Figure 1:
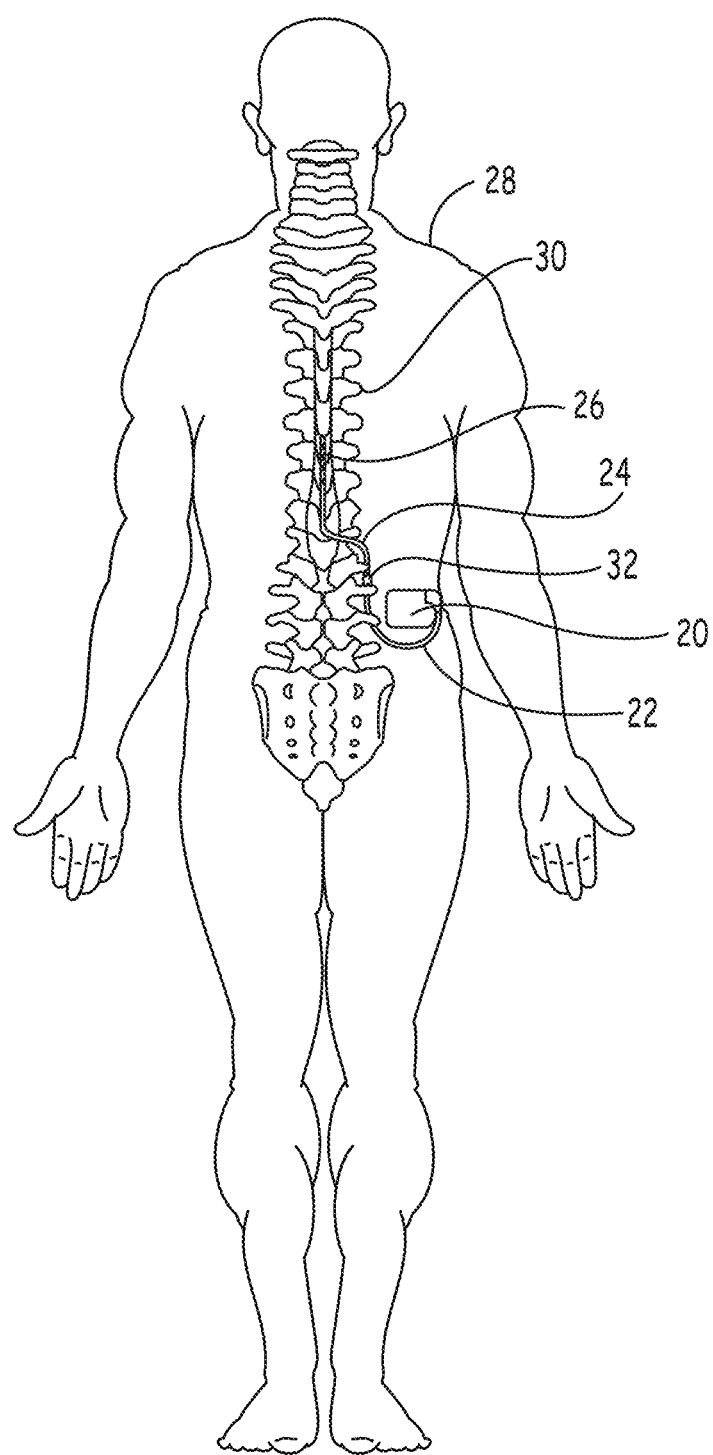
FIG. 1 is a schematic diagram of a an active medical device implanted within a human body.

The figures are not necessarily to scale. Dashed or broken lines indicate internal structure or structure covered by solid surfaces. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to an implantable medical device having a hermetic housing with an internal connector assembly that extends into the hermetic housing. In particular the present disclosure relates to an implantable medical device having an elongate lead connector extending into the hermetic cavity of the device. An open end of the elongate lead connector extends through the hermetic housing and is hermetically joined to the hermetic housing. The elongate lead connector forms a hermetic barrier. The connector concept described herein can be manufactured as a device component with a standardized method of attachment and does not require substantial resources with new device designs improving new device introduction cadence. While the present disclosure is not so limited, an appreciation of various aspects of the disclosure will be gained through a discussion of the examples provided below.

FIG. 1 is a schematic diagram of an active medical device 20 implanted within a human body of patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30.

In many embodiments, the active medical device 20 has on or two leads each having four to eight electrodes or more electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

In many embodiments, each lead 24 is a wire having insulation thereon and includes one or more insulated electrical conductors each coupled at their proximal end to a connector ring and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). In some embodiments, each lead 24 may contain a paddle shape at its distant end for housing electrodes 26. In many embodiments, electrodes 26 may include one or more ring contacts at the distal end of lead 24.

FIG. 2A is a schematic perspective view of an illustrative elongate lead connector 110. FIG. 2B is a schematic perspective view of an illustrative hermetic housing 120 of an implantable active medical device. FIG. 2C is a schematic perspective view of the illustrative elongate lead connector 110 of FIG. 2A assembled into the hermetic housing 120 of an implantable active medical device 100 of FIG. 2B.

In many embodiments, an implantable active medical device 100 includes a hermetic housing 120 defining an exterior surface 122 and a hermetic cavity 129 of an implantable active medical device 100. An elongate lead connector 110 extends into the hermetic cavity 129. The hermetic cavity is defined by the interior surface of the hermetic housing 120. The elongate lead connector 110 includes a closed end 112, an open end 114 extending through and hermetically joined to the hermetic housing 122. An outer surface 116 of the elongate lead connector 110 at least partially defines the hermetic cavity 129, and an inner surface 118 of the elongate lead connector 110 defines a lead aperture or lead receptacle. For ease of illustration, the internal parts of the elongate lead connector 110 are shown in dashed or broken lines. In many embodiments, the elongate lead connector 110 has a connector volume and the hermetic cavity volume is reduced by an amount substantially equal to the connector volume when the elongate lead connector 110 is assembled into the implantable active medical device 100. In other words, the elongate lead connector 110 extends into the hermetic cavity 129 of the hermetic housing 120 and a substantial majority (at least 50% or at least 75%) of the outer surface 116 of the elongate lead connector 110 defines a portion of the hermetic cavity 129.

The hermetic housing 120 exterior surface 122 includes a first major surface 124 and an opposing second major surface 126 and a side surface 125 extending between the first major surface 124 and the second major surface 126. In many embodiments, the hermetic housing 120 exterior surface 122 defines a generally rounded rectangular body, as illustrated in FIG. 2C. In these embodiments, the first major surface 124 and the second major surface 126 can be parallel with each other and formed from two housing shells welded together along a weld line along the side surface 125.

In many embodiments the elongate lead connector 110 open end 114 extends through the side surface 125 of the hermetic housing 120 exterior surface 122, as illustrated in FIG. 2C. In many embodiments the elongate lead connector 110 is disposed between the first major surface 124 and the second major surface 126. In many embodiments the elongate lead connector 110 is surrounded on all sides except for the open end 114 by the hermetic housing 120 exterior surface 122.

The elongate lead connector 110 can include a rigid sleeve 116 disposed about a plurality of contacts 150 and insulating rings 140. The plurality of contacts 150 and insulating rings 140 can be arranged in axial alignment to form the inner surface 118 of the elongate lead connector 110 defining a lead aperture or lead receptacle. An open end 114 of the rigid sleeve 116 can be hermetically fixed to the hermetic housing 120 at the housing aperture 127. The rigid sleeve 116 includes a plurality of electrical contact feedthroughs 55 extending through the rigid sleeve 116 to directly electrically connect the plurality of contacts 150 with the circuit board 50. The feedthroughs may also be in the form of an array assembly or a co-fire feedthrough array.

FIGS. 3A-3E are schematic perspective views of a method of forming an elongate internal connector 110 and disposing it within a hermetic cavity 129 of the implantable active medical device 100. FIG. 3E illustrates the hermetic housing 120 with a either the first major surface 124 or the second major surface 126 removed for ease of illustration of the hermetic cavity 129 and elongate lead connector 110 placement within the same.

In FIGS. 3A-3E, the process of forming the elongate lead connector 110 includes the steps (1)-(5): FIG. 3A or step (1) is the assembly of the feedthroughs (including insulating potting material around each electrically conducting feedthrough 55) to the rigid sleeve first part 116; FIG. 3B or step (2) is loading the alternating contact rings 150 and insulating rings 140 in axial alignment to form the lead aperture 118 onto a nonconductive carrier 160; FIG. 3C or step (3) is placing the loaded carrier onto the rigid sleeve first part 116; FIG. 3D or step (4) is joining each contact ring to its respective feedthrough contact 55 such as by laser or resistance welding and assembling the second part rigid sleeve 116 onto the loaded carrier and rigid sleeve first part and then welding the rigid sleeves together to form the hermetic elongate lead connector 110; and FIG. 3E or step (5) is hermetically fixing the elongate lead connector 110 to the hermetic housing 120 at the housing aperture 127 so that the open end 114 of the rigid sleeve 116 extends through the hermetic housing 120. The electronics can be fixed to the feedthrough contacts 55 and the remaining cover or portion of the hermetic housing 120 is welded together with the assembly shown in step (5) to form the completed implantable active medical device 100.

In many embodiments the implantable active medical device 100 includes electronics disposed within the hermetic housing. Electronics can be any useful electronics such as a circuit board. A circuit board can include both a printed circuit board (often a rigid printed circuit board) and a flexible circuit (also known as a flex circuit), or a combination of a printed circuit board and a flex circuit. In many embodiments a circuit board is fixed to the elongate lead connector 110 via contacts 55 and the circuit board 50 is disposed within the hermetic housing as illustrated in FIG. 2C. The circuit board may also be rigidly fixed to the elongate lead connector by for example screws, clips, or other means. The hermetic housing defines a hermetic cavity. In many embodiments the hermetic housing is a metallic shell.

In many embodiments the elongate lead connector 110 is fixed to the circuit board via direct electrical connections 55 between the elongate lead connector 110 and the circuit board as illustrated in FIG. 2C. The electronics generally control the active medical device. In some embodiments, the electronics includes memory. The memory can be any magnetic, electronic, or optical media, such as random access memory (RAM), read-only memory (ROM), electronically-erasable programmable ROM, flash memory, or the like.

In many embodiments the elongate lead connector 110 is fixed at only one end (proximal or open end 114) to the hermetic housing 120. In these embodiments, the elongate lead connector 110 is in cantilever arrangement within the hermetic housing 120.

In many embodiments the implantable active medical device 100 includes a power source 60 disposed within the hermetic housing 120. The power source 60 can include a battery, for example disposed within a hermetic housing, shield or shell. The power source 60 can be electrically connected to the circuit board 50 via electrical connections such as soldering or welding. The power source 60 can be any useful battery or inductive coil.

The illustrated lead connector 110 is an elongated member extending between a lead aperture 114 open end and an end cap or closed end 112, and having an inner surface defining an open lumen lead aperture 118. The elongate lead connector defines at least a portion of the hermetic barrier. The lead connector can be utilized to provide the hermetic barrier extending into a device.

In many embodiments, the lead connector 110 includes two or more electrically conducting contact rings 150 spaced apart by electrically insulating rings 140. The two or more electrically conducting contact rings 150 provide electrical communication between the electronics or circuit board 50 and the lead contact. The lead connector 110 provides a hermetic seal between the hermetic housing cavity 129 and the lead aperture 118.

The electrically conducting contact rings can be formed of any useful electrically conductive material. In many embodiments, the electrically conducting contact rings are formed of a metallic material such as, for example, titanium, stainless steel, MP35N, niobium, tantalum, platinum, and alloys or combinations thereof. In some embodiments, the electrically conducting contact rings are formed of a metallic material such as, for example, titanium.

The electrically insulating material 140 can be formed of any useful electrically flexible insulating material. In many embodiments the electrically insulating material 140 is liquid silicone rubber formed in such a configuration to provide electrical isolation between adjacent contact rings.

In some embodiments, a filtering capacitor is disposed between each electrically conducting contact rings 150 and the electronics 50. The filtering capacitor can effectively filter out undesirable electromagnetic interference (EMI) from the active medical device 100.

Placement of the lead connector 110 within the hermetically sealed active medical device housing enables a direct electrical connection between the lead connector 110 and the electronics 50. In addition, the elimination of a traditional feedthrough through the device housing 120 can reduce the size and volume of the implantable active medical device and can also reduce the number of parts and connections needed to assemble the implantable active medical device. Also, the method of attachment of the lead connector to the device housing is substantially simplified and the lead connector is isolated from external loading The illustrated lead connector 110 is an elongate member extending between a lead aperture 118 first open end 114 and a closed end or end cap 112, and having an inner surface defining an open lumen lead aperture 118. The open lumen lead aperture 118 or lead receptacle 118 is configured to accept one lead or lead extension, as described above, and electrically couple one or more lead contacts with one or more connector contacts 150 nested in the elongate body of the lead connector 110, that in many embodiments is generally cylindrical.

In many embodiments, substantially the entire lead connector outer surface 116 is disposed within the hermetic cavity 129 and at least partially defines the hermetic cavity. In some embodiments, the entire lead connector outer surface 116 is disposed within the hermetic cavity 129.

A mounting flange 119 can be fixed to the lead connector 110 adjacent the open end 114. The mounting flange 119 can be hermetically fixed to the hermetic housing 120 via braze or weld joint. A retention member (not shown) such as for example, a set screw, can be disposed on the lead connector 110 adjacent to the open end 114 and can assist in mechanical retention of the lead disposed within the lead aperture 118.

Thus, embodiments of the IMPLANTABLE DEVICE WITH INTERNAL LEAD CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. An implantable active medical device comprising:
a hermetic housing defining an exterior surface and a hermetic cavity of an implantable active medical device;
an elongate lead connector comprising a rigid sleeve and forms a hermetic barrier extending into the hermetic cavity through the hermetic housing, wherein the elongate lead connector comprises a closed end, an open end extending through and hermetically joined to the hermetic housing, an outer surface at least partially defining the hermetic cavity, and an inner surface defining a lead aperture configured to accept one of a lead or a lead extension, wherein the open end is an open end of the rigid sleeve hermetically fixed to the hermetic housing, wherein the rigid sleeve is surrounded on all sides by the hermetic housing exterior surface; and
a circuit board disposed within the hermetic cavity and directly coupled to the elongate lead connector.

2. The implantable active medical device according to claim 1, wherein the hermetic housing exterior surface comprises a first major surface and an opposing second major surface and a side surface extending between the first major surface and the second major surface.

3. The implantable active medical device according to claim 2, wherein the elongate lead connector open end extends through the side surface.

4. The implantable active medical device according to claim 2, wherein the elongate lead connector is disposed between the first major surface and the second major surface.

5. The implantable active medical device according to claim 1, wherein the elongate lead connector is surrounded on all sides, except for the open end, by the hermetic housing exterior surface.

6. The implantable active medical device according to claim 1, further comprising a power source disposed within the hermetic cavity.

7. The implantable active medical device according to claim 1, wherein the rigid sleeve disposed about a plurality of contacts and insulating sealing rings.

8. The implantable active medical device according to claim 7, wherein the rigid sleeve comprises a plurality of electrical contact feedthroughs extending through the rigid sleeve to directly electrically connect the plurality of contacts with a circuit board or device electronics.

9. An implantable active medical device comprising:
a hermetic housing defining an exterior surface, a hermetic cavity volume of an implantable active medical device, and a housing aperture extending through the exterior surface to the hermetic cavity volume;
an elongate lead connector forming a hermetic barrier and comprising a sleeve extending into the hermetic cavity from the exterior surface at the housing aperture, the elongate lead connector comprises a closed end, an open end of the sleeve extending through and hermetically joined to the hermetic housing, an outer surface, and an inner surface defining a lead aperture configured to accept one of a lead or a lead extension; and
a circuit board disposed within the hermetic cavity and coupled to the elongate lead connector;
wherein the elongate lead connector has a connector volume and the hermetic cavity volume is reduced by an amount substantially equal to the connector volume when the elongate lead connector is assembled into the implantable active medical device.

10. The implantable active medical device according to claim 9, wherein the circuit board is electrically connected to the elongate lead connector and this electrical connection does not pass through the hermetic housing.

11. The implantable active medical device according to claim 9, further comprising a power source disposed within the hermetic cavity.

12. The implantable active medical device according to claim 9, wherein the elongate lead connector comprises a rigid sleeve disposed about a plurality of contacts and insulating sealing rings and an open end of the rigid sleeve is hermetically fixed to the hermetic housing.

13. The implantable active medical device according to claim 12, wherein the rigid sleeve comprises a plurality of electrical contact feedthroughs extending through the rigid sleeve to directly electrically connect the plurality of contacts with a circuit board.

14. The implantable active medical device according to claim 9, wherein the hermetic housing exterior surface comprises a first major surface and an opposing second major surface and a side surface extending between the first major surface and the second major surface.

15. The implantable active medical device according to claim 14, wherein the elongate lead connector open end extends through the side surface.

16. The implantable active medical device according to claim 14, wherein the elongate lead connector is disposed between the first major surface and the second major surface.

* * * * *